(12) United States Patent  (10) Patent No.: US 8,214,164 B2
Gandhi et al.  (45) Date of Patent: Jul. 3, 2012

(54) ABNORMAL BATTERY DEPLETION DETECTION IN AN IMPLANTABLE DEVICE

(75) Inventors: Rajesh K. Gandhi, Woodbury, MN (US); William J. Linder, Golden Valley, MN (US); Scott Vanderlinde, Plymouth, MN (US); James Kalgren, Lino Lakes, MN (US); Hal M. Propp, Oakdale, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 562 days.

(21) Appl. No.: 12/277,091

(22) Filed: Nov. 24, 2008

(65) Prior Publication Data

US 2009/0182517 A1 Jul. 16, 2009

Related U.S. Application Data

(60) Provisional application No. 61/007,636, filed on Dec. 13, 2007.

(51) Int. Cl.
*G01R 31/36* (2006.01)
(52) U.S. Cl. .......... 702/58; 324/433; 320/132; 320/136; 702/63
(58) Field of Classification Search .................. 702/63, 702/64, 57, 185, 199; 324/320, 433
See application file for complete search history.

(56) References Cited

U.S. PATENT DOCUMENTS

| | | | |
|---|---|---|---|
| 4,332,256 A | 6/1982 | Brownlee et al. | |
| 4,416,282 A | 11/1983 | Saulson et al. | |
| 4,556,061 A | 12/1985 | Barreras et al. | |
| 4,715,381 A | 12/1987 | Moberg | |
| 5,031,616 A * | 7/1991 | Mann et al. | 607/11 |
| 5,137,020 A | 8/1992 | Wayne et al. | |
| 5,313,953 A * | 5/1994 | Yomtov et al. | 600/508 |
| 5,325,041 A | 6/1994 | Briggs | |
| 5,344,431 A | 9/1994 | Merritt et al. | |
| 5,391,193 A | 2/1995 | Thompson | |
| 5,432,429 A * | 7/1995 | Armstrong et al. | 320/136 |
| 5,458,624 A | 10/1995 | Renirie et al. | |
| 5,620,474 A | 4/1997 | Koppman | |
| 5,713,936 A | 2/1998 | Staub | |

(Continued)

FOREIGN PATENT DOCUMENTS

EP 1038498 A2 9/2000

(Continued)

OTHER PUBLICATIONS

"International Application Serial No. PCT/US2008/013059, International Search Report mailed May 27, 2009", 4 pgs.

(Continued)

*Primary Examiner* — Andrew Schechter
*Assistant Examiner* — Haidong Zhang
(74) *Attorney, Agent, or Firm* — Schwegman, Lundberg & Woessner, P.A.

(57) ABSTRACT

Abnormal battery depletion can be detected in an implantable medical device. Battery capacity consumed can be measured using a coulometer and using a capacity-by-voltage device, and the measurements can be blended to determine battery status. A drop in battery voltage below a specified threshold can be detected to identify a high-current depletion fault, and an alarm can be provided to indicate the fault has been detected. The specified threshold can be determined as a function of battery capacity consumed. Other aspects and embodiments are provided herein.

21 Claims, 12 Drawing Sheets

U.S. PATENT DOCUMENTS

| | | |
|---|---|---|
| 5,741,307 A | 4/1998 | Kroll |
| 5,769,873 A | 6/1998 | Zadech |
| 5,800,472 A | 9/1998 | Mann |
| 5,904,705 A | 5/1999 | Kroll et al. |
| 5,931,791 A | 8/1999 | Saltzstein et al. |
| 6,108,579 A | 8/2000 | Snell et al. |
| 6,148,235 A | 11/2000 | Kuiper |
| 6,167,309 A | 12/2000 | Lyden |
| 6,185,461 B1 | 2/2001 | Er |
| 6,400,988 B1 | 6/2002 | Gurewitsch |
| 6,438,409 B1 | 8/2002 | Malik et al. |
| 6,531,874 B2 * | 3/2003 | Mentgen et al. .............. 324/427 |
| 6,671,552 B2 | 12/2003 | Merritt et al. |
| 6,760,625 B1 | 7/2004 | Kroll |
| 6,885,894 B2 | 4/2005 | Stessman |
| 6,901,293 B2 | 5/2005 | Rogers et al. |
| 6,940,255 B2 | 9/2005 | Loch |
| 7,058,451 B2 | 6/2006 | Obel et al. |
| 7,072,725 B2 | 7/2006 | Bristol et al. |
| 7,177,690 B2 | 2/2007 | Woods et al. |
| 7,194,308 B2 | 3/2007 | Krig et al. |
| 7,221,977 B1 | 5/2007 | Weaver et al. |
| 7,239,146 B2 | 7/2007 | James et al. |
| 2001/0034541 A1 | 10/2001 | Lyden |
| 2002/0143580 A1 | 10/2002 | Bristol et al. |
| 2003/0065366 A1 | 4/2003 | Merritt et al. |
| 2004/0039424 A1 | 2/2004 | Merritt et al. |
| 2004/0199146 A1 | 10/2004 | Rogers et al. |
| 2005/0102005 A1 * | 5/2005 | Krig et al. ....................... 607/29 |
| 2005/0256548 A1 | 11/2005 | Rogers et al. |
| 2005/0266301 A1 * | 12/2005 | Smith et al. ..................... 429/61 |
| 2005/0277994 A1 | 12/2005 | McNamee et al. |
| 2006/0176022 A1 * | 8/2006 | Namba ......................... 320/130 |
| 2006/0220619 A1 * | 10/2006 | Namba et al. ................. 320/149 |
| 2007/0150018 A1 | 6/2007 | Betzold et al. |
| 2008/0097544 A1 | 4/2008 | Gandhi et al. |
| 2009/0312809 A1 | 12/2009 | Gandhi et al. |

FOREIGN PATENT DOCUMENTS

| | | |
|---|---|---|
| EP | 1610437 A1 | 12/2005 |
| WO | WO-01/05466 A1 | 1/2001 |
| WO | WO-01/08749 A1 | 2/2001 |
| WO | WO-02/49718 A1 | 6/2002 |
| WO | WO-2004/091697 A1 | 10/2004 |

OTHER PUBLICATIONS

"International Application Serial No. PCT/US2008/013059, Written Opinion mailed May 27, 2009", 7 pgs.

* cited by examiner

FIG. 8C

ABNORMAL BATTERY DEPLETION DETECTION IN AN IMPLANTABLE DEVICE

CROSS REFERENCE TO RELATED APPLICATION

This application claims the benefit of provisional U.S. patent application Ser. No. 61/007,636, filed on Dec. 13, 2007, which is hereby incorporated by reference in its entirety.

This application is related to the following commonly assigned U.S. patent application which is herein incorporated by reference in its entirety: "Dynamic Battery Management in an Implantable Device," Ser. No. 11/551,269, filed Oct. 20, 2006.

TECHNICAL FIELD

This disclosure relates generally to implantable devices, and more particularly to systems and methods for abnormal battery depletion detection in an implantable device.

BACKGROUND

Implantable medical devices include, among other things, cardiac rhythm management (CRM) devices such as pacers, cardioverters, defibrillators, cardiac resynchronization therapy (CRT) devices, as well as combination devices that provide more than one of these therapy modalities to a subject. Such implantable devices are typically powered by a battery. When the battery's useful life has been exhausted, the implanted device is typically explanted and replaced before the cessation of therapy. Therefore, it is often useful to know how much battery capacity has been used and/or how much battery capacity remains.

SUMMARY

The present inventors have recognized, among other things, that during device operation, high-current depletion faults can cause battery voltage to decrease. The present inventors have recognized that improved systems and methods for battery management and abnormal battery depletion detection in implantable medical devices are needed. The above-mentioned problems and others not expressly discussed herein are addressed by the present subject matter and will be understood by reading and studying this specification.

Disclosed herein, among other things, is a method for abnormal battery depletion detection in an implantable medical device. In an example, battery capacity consumed can be measured using a coulometer and using a capacity-by-voltage device, and these two different types of measurements are blended to determine battery status. A drop in battery voltage below a specified threshold can be detected to identify a high-current depletion fault, and an alarm can be provided to indicate the fault has been detected, in an example. The specified threshold can be determined as a function of battery capacity consumed.

Another aspect of this disclosure relates to a system for abnormal depletion detection in an implantable device. An example of the system includes a coulometer configured to measure battery capacity and a capacity-by-voltage device configured to use a sensed battery voltage to measure battery capacity. A controller connected to the coulometer and the capacity-by-voltage device can be configured to combine the measurements from the coulometer and the capacity-by-voltage device, using a weighted average to determine battery capacity consumed. The controller can be configured to detect a drop in the sensed battery voltage below a specified threshold to identify a high-current depletion fault and to provide an alarm to indicate the fault has been detected. The specified threshold can be determined as a function of battery capacity consumed as computed using the weighted average.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

FIGS. 8A-8E illustrate screen displays for the system of FIG. 3, used to display battery longevity, in an example.

DETAILED DESCRIPTION

Various examples of the present subject matter are related to implantable medical device battery management. Displaying the remaining battery capacity in ampere-hours can cause a misunderstanding by users, as users may believe it represents the amount of time remaining rather than the amount of charge remaining.

In an example, the present subject matter includes a system for measuring consumed battery capacity. In an example, this system includes blending multiple different types of measurements of battery capacity. In an example, the system includes a display and battery longevity can be displayed in units of time left in the life of the battery. The present disclosure can be used with a variety of implantable device batteries, including by not limited to: SVO (Silver Vanadium Pentoxide), $MnO_2$ (Lithium Manganese Dioxide), CFx (Lithium Carbon Monofluoride) and hybrid SVO and CFx batteries.

Examples of System for Dynamic Battery Management

Figure 1:
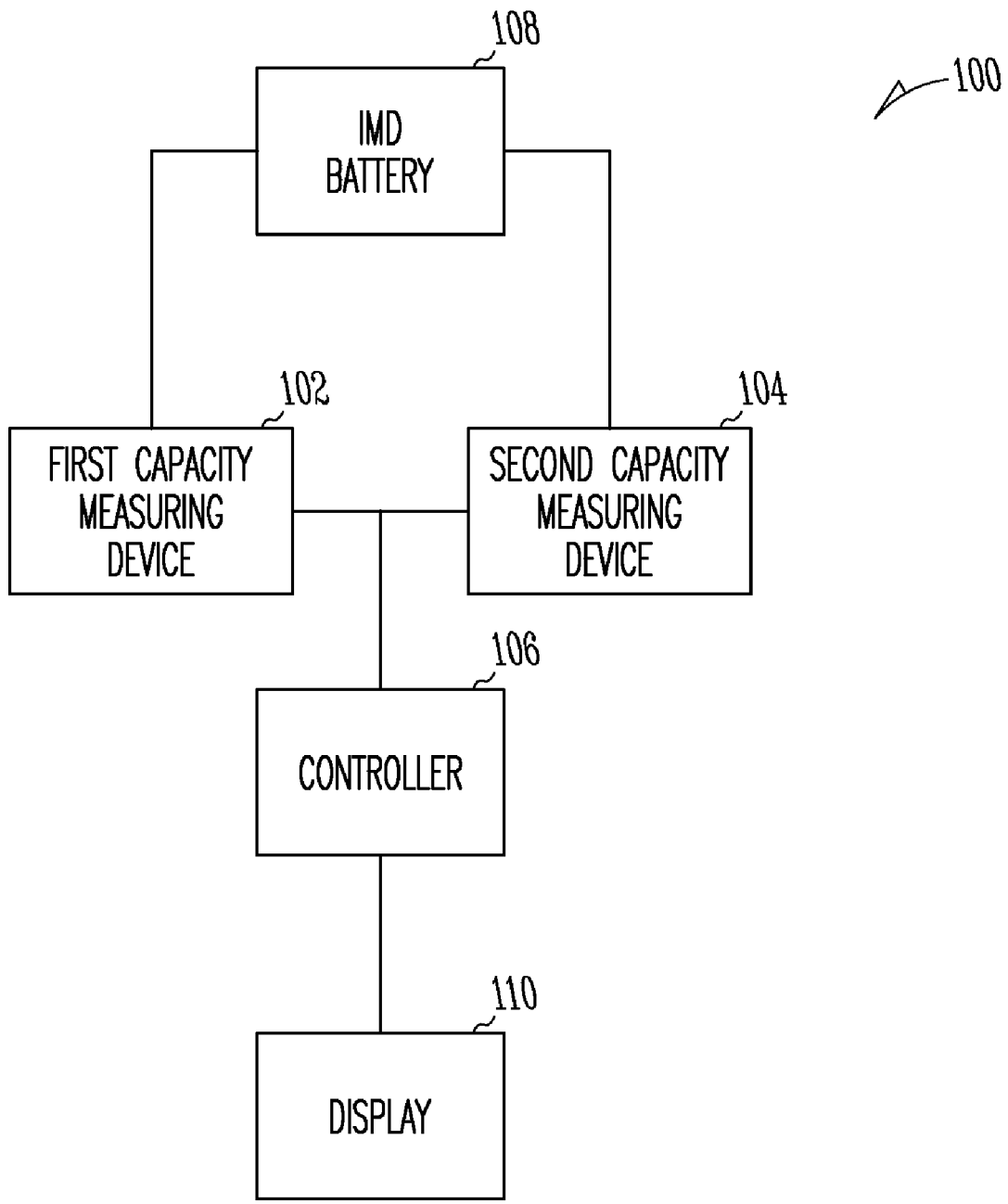
FIG. 1 illustrates a block diagram of a system for dynamic battery management, in an example.

FIG. 1 illustrates a block diagram of a system for dynamic battery management, in an example. An example of the system 100 includes two or more devices (102, 104) for measuring battery capacity for an implantable medical device battery 108. The example also includes a controller 106 connected to the measuring devices. The controller 106 can be configured to combine the measurements from the measuring devices (102, 104), such as by using a weighted average to determine battery capacity consumed. In an example, at least one of the measuring devices includes a coulometer (or Coulomb counter), which can measure or estimate the amount of charge that has been delivered from the battery. At least one of the measuring devices includes a capacity-by-voltage device, in an example. A capacity-by-voltage device can detect a battery terminal voltage level, which can be used to compute and output a battery capacity using, for instance, a look-up table. In an example, at least one of the measuring devices includes a software-assisted coulometer. In an example, the software-assisted coulometer can tally various system events (such as a shock or pace sequence), duration and amplitude of the event, and can multiply (such as by using a look-up table) the corresponding cost (energy used in ampere-hours). The accumulation of events, duration and cost would result in accumulated capacity consumed, which can be expressed in units of ampere·hours (A·hr). In certain examples, at least one of the measuring devices includes a charge-time measuring device. A charge-time measuring device can be particularly useful when used in a system including a defibrillator, because in a defibrillator system, the defibrillation output capacitor charging time can directly be related to battery internal impedance. The voltage drop from open-circuit to loaded for a high voltage (HV) defibrillation capacitor charge divided by the loaded current represents a measure of the internal battery impedance ($R=\Delta V/\Delta I$). From a look-up table or other technique, the internal battery impedance can be mapped to capacity consumed, in an example. The system further includes a display 110 in communication with the controller 106 in an example. The display 110 can be configured to provide a depiction of battery longevity, such as in units of time remaining in the life of the implantable medical device battery, in an example.

In an example, the system of FIG. 1 can be configured to dynamically manage an implanted device. In a contrasting approach, a static explant capacity can be allocated at design-time for a heavy usage scenario (e.g., 5% of a device's battery capacity will remain at the explant indicator, or elective replacement indicator (ERI)). That battery capacity can be designed to offer at least 90 days of heavy usage therapy before cessation. In the present system, using dynamic allocation, the device actively measures long-term power consumption and accordingly allocates post-explant-indicator battery capacity. In this manner, low-usage devices will have less reserve capacity but longer total longevity. High-usage devices will have more post-explant-indicator reserve capacity and less total longevity. This strategy can increase or maximize individual implantable device longevity and can decrease or minimize risk of therapy cessation before implantable device replacement.

When using a capacity-by-voltage device, a look-up table can be indexed by power and battery terminal voltage to obtain battery capacity consumed, in an example. The capacity-by-voltage device uses at least one voltage measuring device, in an example. In certain examples, accuracy of the capacity-by-voltage device is best near ERI, but may be unusable before significant (approximately 30%) battery depletion, because many batteries have flat or even rising battery terminal voltage profiles early in the battery life (see FIG. 7, discussed below).

When using a coulometer, or Coulomb counter, the device can include one of a number of different devices, such as to measure voltage across a known resistance and compute a battery current therefrom. The current can be integrated over time with a result of amp-seconds, or coulombs, a measure of charge. Capacity consumed can be measured constantly or on an ongoing recurrent basis by the coulometer, in an example. In an example, the coulometer can be calibrated to an accuracy of +/−10% or better. Absolute accuracy of the coulometer can be most useful early in battery life.

Figure 5:
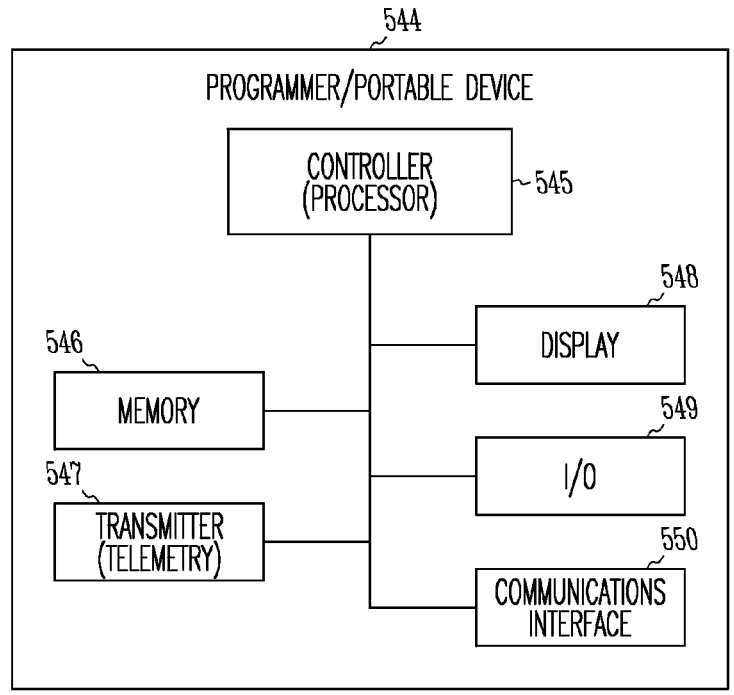
FIG. 5 illustrates a block diagram of a programmer such as illustrated in the system of FIG. 4 or other external device to communicate with the IMD(s), in an example.

In an example, the capacity measuring devices (102, 104) are located within the implantable medical device (IMD). In an example, the controller can be located within the IMD. In this example, measurement and blending of the measured data are completed within the IMD, and both raw and blended data are reported to an external device having display 110. An example of the external device is shown in FIG. 5. In an example, the depiction of battery longevity provided by the display includes a semicircular gauge or the like. In another example, the depiction of battery longevity includes a bar, line or other graph or the like.

Figure 2:
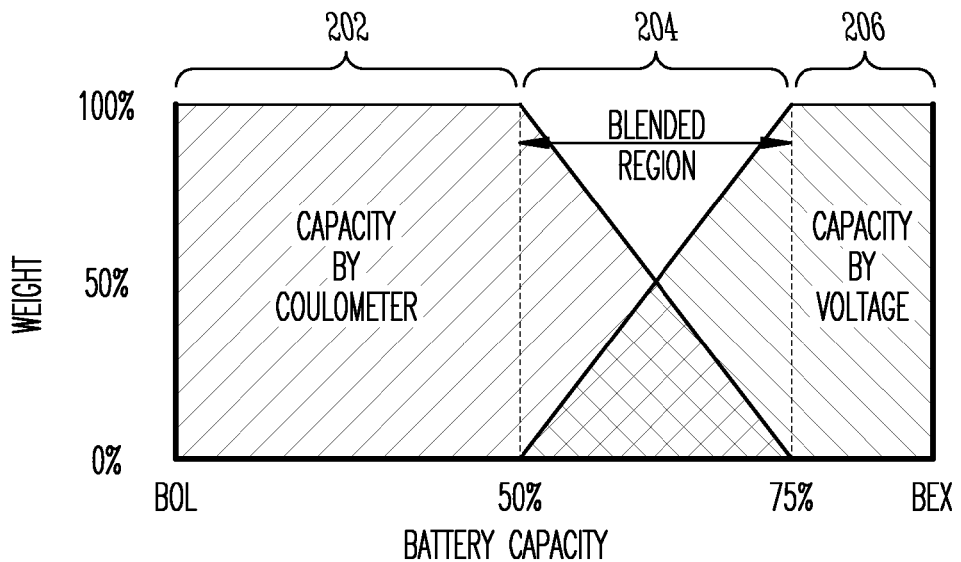
FIG. 2 illustrates a graphical diagram of blended battery capacity for an implantable medical device, in an example.

FIG. 2 illustrates a graphical diagram of blended battery capacity for an implantable medical device, in an example. Over a first portion 202 of the life of the battery, battery capacity consumed can be measured using a first capacity measuring device (e.g., a coulometer). Measurements from the coulometer and measurements of battery capacity consumed using a second capacity measuring device (e.g., a capacity-by-voltage device) are combined (or capacity-blended) over a second portion of the life of the battery 204. Battery capacity consumed can be measured using only the capacity-by-voltage device over a third portion of the life of the battery 206, in an example.

Figure 7:
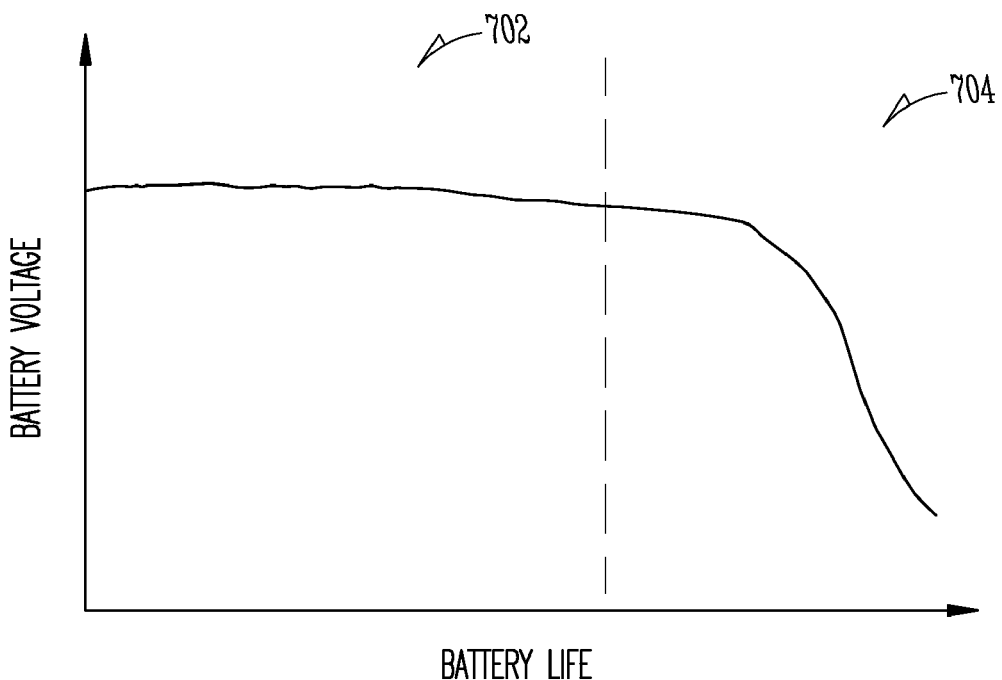
FIG. 7 illustrates a graphical diagram of measured voltage over the life of a battery, in an example.

Battery capacity consumed can be measured relatively directly with the coulometer and relatively indirectly by measuring battery voltage. A mapping can be used between voltage measured and capacity consumed, in certain examples. FIG. 7 illustrates a graphical diagram of measured battery voltage over the life of a battery, in an example. As shown in this example, the coulometer method can be better suited for the early portion 702 of the battery's life, where battery voltage measurement technique provides less resolution. The battery voltage measurement method can be better suited for the later portion 704 of the battery's life, in this example.

As shown in FIG. 2, discussed above, measurements of battery capacity derived from the coulometer and measurements of battery capacity derived from the capacity-by-voltage device are "capacity-blended" over a time period. In certain examples, capacity-blending uses a weighted average of the outputs of two or more battery capacity measuring devices to calculate battery capacity. Capacity-blending the measurements largely reduces abrupt changes in longevity gauge behavior. In the example of FIG. 2, at approximately 51% capacity consumed (as measured by the coulometer), blending of the measurements begins. A weighted average can be computed to combine the measurements from the coulometer and the capacity-by-voltage device, in an example. In an example, at 51% capacity consumed, the combination includes 99% of the coulometer measurement and 1% of the capacity-by-voltage measurement, at 62.5% capacity consumed, the combination includes 50% of the coulometer measurement and 50% of the capacity-by-voltage measurement, and at 74% capacity consumed, the combination includes 1% of the coulometer measurement and 99% of the capacity-by-voltage measurement, and in between these points the percentage of each measurement used can be linearly interpolated. Other techniques for combining or capacity-blending the coulometer and capacity-by-voltage measurements of battery capacity are possible, without departing from the scope of this disclosure. In addition, more than two sources of battery capacity measurements can be combined in this manner, such as software coulometer capacity measurements and charge-time capacity measurements.

In an example, the system calculates life phase from total capacity, based on measured capacity consumed, average power consumption rate, and a set of constants or other parameters. The coulometer can be used to measure power, in an example. In an example, the coulometer measures capacity in units of Ampere·seconds. The difference between two coulometer measurements over a time period can be divided by the duration of the time period, and the result is average battery current (in amperes). Multiplying the average battery current by the average (or most recently-measured) battery voltage yields average battery power. Long-term average battery power can be used to filter individual battery power measurements, such as a simple average, a moving average, or other measure of central tendency. In an example, battery life phases calculated include, but are not limited to: BOL (beginning of life), OY (one year remaining to explant, Explant (90 days until EOL), ERI (elective replacement indicator, usually the same as Explant), EOL (end of life), and BEX (battery expired). Based on total capacity of the battery model (Qbex) and desired duration of each life phase, indicator trigger points are computed (using the formula t=Q×V/P). For example, if a 90 day period from BOL to BEX is desired, V and P can be measured and Q calculated. Subtracting that value from Qbex yields Qeol. Similarly, if a 150 day period is desired from ERI to EOL, Qeol and Qeri can be calculated. Life phase can then be triggered by comparing the most recent blended capacity (Qi) to the trigger capacity. For example, if Qi>Qeri, then a message indicating ERI can be displayed. While this example uses a capacity based system, voltage and charge time can be used without departing from the scope of this disclosure. For fault control, voltage, power and charge time limits exist. In an example, measuring battery capacity consumed includes measuring battery capacity in units of Ampere·hours (Ahr). In an example, capacity from a capacity-by-voltage device ($Q_{voltage}$) and capacity from a coulometer ($Q_{coulometer}$) are capacity-blended using the following technique:

$$Q_i = \frac{Q_{i-1} - \frac{Q_{BEX}}{2}}{75\% \times Q_{BEX} - \frac{Q_{BEX}}{2}} \times Q_{Voltage} + \left(1 - \frac{Q_{i-1} - \frac{Q_{BEX}}{2}}{75\% \times Q_{BEX} - \frac{Q_{BEX}}{2}}\right) \times Q_{Coulometer}$$

Other techniques for combining or capacity-blending the coulometer and capacity-by-voltage measurements of battery capacity are possible, without departing from the scope of this disclosure.

In an example, the implantable medical device (IMD) measures capacity consumed, average power and voltage, and calculates trip points for BEX, EOL, ERI and OY. The IMD compares capacity consumed to capacity trip points to determine life phase, in an example. In an example, three of three consecutive calculations over a trip point will trigger a life phase status change, which can be accompanied by an indicator or alert. Three calculations are used in this example to filter noise. More or fewer calculations can be used to trigger a life phase status change, such as based on the magnitude of the noise and the ability to pre-filter the noise. In an example, the IMD reports certain values to an external device having a display (such as the programmer depicted in FIG. 5). Examples of reported values include Qi, Qeri, P and V. The programmer can then compute time to ERI (or time to explant), and can further estimate IMD battery longevity based on user changes to programming settings such as pace mode, pace pulse width and amplitude, in an example. In an example, time to explant can be calculated with an extra allocation for power consumed by subsequent defibrillation capacitor reform operations. Reforming a capacitor refers to recharging the capacitor to avoid leakage currents. Time to explant can be recalculated if the IMD is reprogrammed (amplitude, pulse width, etc.), in an example.

In an example, a hardware-based coulometer can be used to monitor power consumption over a specified time interval. Based on these measurements, one or more power alarms can be provided. Before implant, if the IMD exceeds a power consumption limit (75 µW over 1 week, for example) for three measurements in a row, a battery fault condition can be declared and the clinician can be instructed not to implant the device, in an example. In an example, if the device exceeds one or more fixed power limits, such as over 20 seconds or 1 day in pre-implant testing, for example, an alarm can be set. Post-implant, if the device exceeds an expected power, such as over 20 seconds, 1 day, or 1 week, an alarm can be set in an example. Alarms are logged by the device but not displayed, in an example.

An example of the system includes a coulometer configured to measure battery capacity consumed in an implantable device. The system example also includes a capacity-by-voltage device configured to measure battery capacity consumed in the device. The system example further includes means for blending the measurements from the coulometer and the capacity-by-voltage device to determine battery capacity consumed. In an example, the means for blending includes a computer processor or controller circuit. The means for blending can also include executable, readable, or otherwise performable instructions tangibly stored in a computer readable medium, in an example.

In an example, the controller can be configured to select respective capacity measurements from the two or more capacity measurement devices, and use only one of the measurements, or to compute a capacity-blended combination of the measurements, based on one or more factors such as: a specified or programmable schedule; one or more specified set points; one or more battery parameters; or one or more battery life indicators.

Certain battery chemistries, CFx and $MnO_2$ in particular, are prone to depressed voltage immediately after a high-power event (e.g., wireless telemetry, beeper actuation, or defibrillation capacitor charging). Because battery terminal voltage can be used to determine battery depletion state, it would be possible to erroneously read a low battery terminal voltage and responsively change the indication of the battery life-phase. In an example, measurement of battery voltage can be automatically inhibited during a high-power event, and the change in battery voltage can be monitored to ascertain when the battery voltage is recovered from the event before the battery voltage measurement is again used to evaluate battery status via measurement by the capacity-by-voltage device.

Before being implanted, the implantable device may be subject to cold temperatures. Depending on battery chemistry and device model, low temperature may cause low monitored battery terminal voltage, long defibrillation capacitor charge time, or inability to communicate via wireless radio frequency (RF) or inductive telemetry. In an example, the device has a temperature detector with one or more built-in temperature limits, such as to generate an alert to warn the user of potentially long charge times or the inability to establish wireless telemetry communications. After the device is implanted, lead impedance, pace counts and sense counts are measured and averaged on a recurrent or periodic basis, in an example. In an example, lead impedance, pace counts and sense counts can be used to predict time to explant and one or more battery terminal voltage or other limits for transiently triggering one or more power alarms.

System for Displaying Battery Longevity

Figure 3:
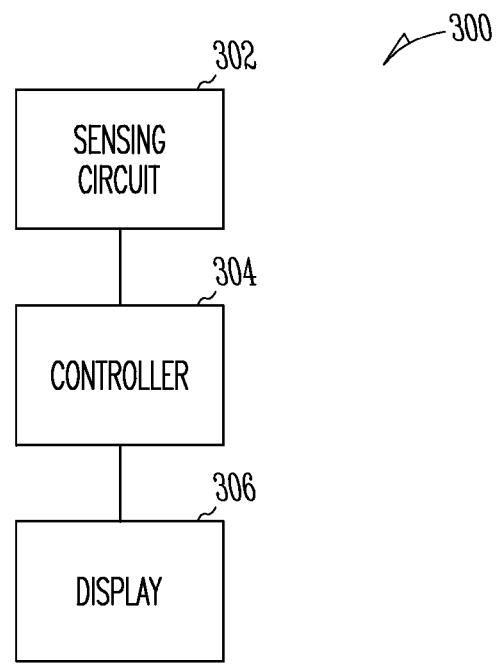
FIG. 3 illustrates a block diagram of a system for displaying battery longevity, in an example.

FIG. 3 illustrates a block diagram of a system for displaying battery longevity, in an example. The system of FIG. 3 can be a subsystem of that depicted in FIG. 1, in an example. In this example, the system 300 includes a sensing sub-system, or sensing circuit 302, configured to measure remaining battery capacity for an implantable device. The system example also includes a controller 304 circuit connected to the sensing circuit 302, or sensing sub-system. The controller 304 can be configured to calculate battery longevity based on measured capacity. The system example further includes a display 306 in communication with the controller 304, the display 306 configured to depict battery longevity shown in units of time remaining in the life of the battery. In an example, the display 306 can be configured to depict a semicircular gauge with battery longevity. In an example, the display 306 can be configured to depict a graph showing battery longevity. Other types of displays showing units of time remaining in the life of the battery are possible without departing from the scope of the disclosure. The system 300 also has the capability to display battery capacity in units of Ahr, in an example.

The display 306 can be part of a programmer, such as depicted in FIG. 5 below, in an example. The sensing circuit 302 can be located within the implantable device, in an example. The controller 304 can be located within the implantable device, within the programmer, or controller function can be shared between the device and programmer in an example. In an example, the controller may be located in a computing system separate from the device and programmer.

In an example, the display depicts battery longevity using a "gas gauge" display, such as including a semi-circle time remaining gauge with a 1-year remaining pie-slice (see FIGS. 8A-8D, discussed below). A "time to explant" gauge can be used in the depicted example. In addition, the display includes numeric capacity remaining and power consumption, in an example. In an example, a graph can be used to depict battery longevity (see FIG. 8E, discussed below). In certain examples, benefits of a time remaining gauge include a full-scale representation of fixed longevity for all devices of the same model number, and that the one-year remaining trigger point on the gauge can be fixed for a given model number. In an example, battery capacity consumed includes battery capacity in units of Ampere·hours (Ahr).

A further example of the system includes means for sensing remaining battery capacity for an implantable device. The system example also includes means for calculating battery longevity based on sensed capacity, the calculating means coupled to the sensing means. The system example further includes a display coupled to the calculating means, the controller and the display cooperate to depict battery longevity in units of time remaining in the life of the battery. In an example, the sensing means includes a coulometer. The sensing means includes a capacity-by-voltage device, in an example. Other types of sensing means can be used without departing from the scope of this disclosure. In an example, the calculating means includes a microprocessor. Other types of calculating means can be used without departing from the scope of this disclosure. The calculating means shown and described herein can be implemented using software, hardware, or combinations of software and hardware.

Implantable Medical Devices

Figure 4:
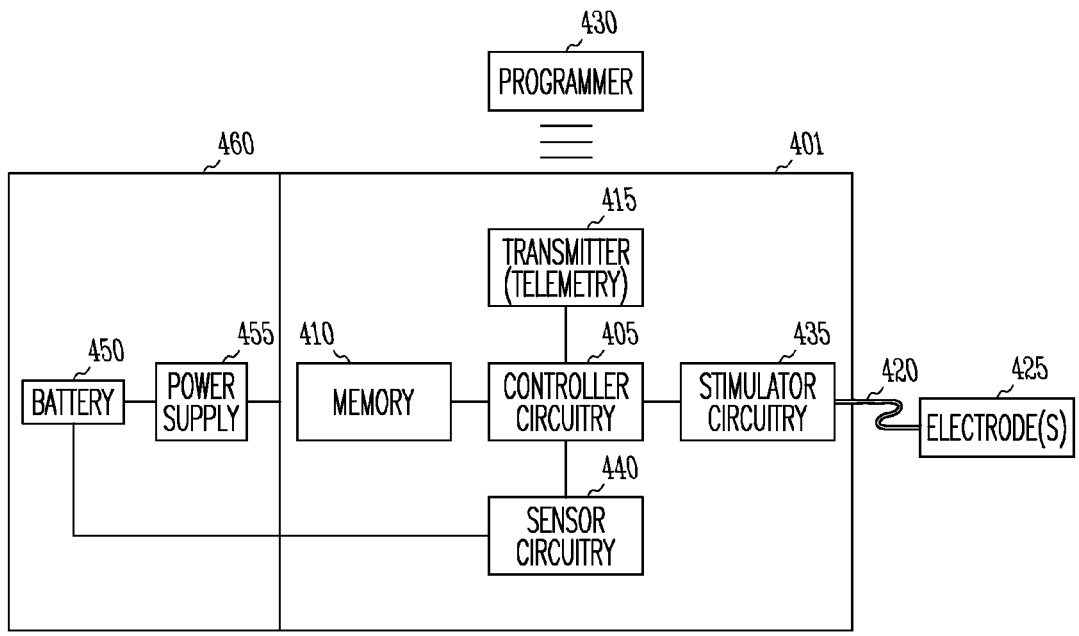
FIG. 4 illustrates a block diagram of a system with an implantable medical device (IMD), in an example.

FIG. 4 illustrates a block diagram of a system with an implantable medical device (IMD), in an example. In this example, the system includes an IMD 401, an electrical lead 420 coupled to the IMD 401, and at least one electrode 425. In this example, the IMD includes a controller circuit 405, a memory circuit 410, a wireless telemetry circuit 415, and a stimulation circuit 435. The controller circuit 405 can perform instructions stored in the memory circuit to control delivery of an electrical stimulation therapy. Therapy can be delivered by the stimulation circuit 435, such as through the lead 420 and the electrode(s) 425. The wireless telemetry circuit 415 allows communication with an external programmer 430 or other external device. The programmer 430 can be used to adjust the programmed therapy provided by the IMD 401, and the IMD can report device data (such as battery capacity remaining and lead resistance) and physiologic or therapy data (such as sense and stimulation data) to the programmer using wireless telemetry, for example. The illustrated system also includes sensor circuitry 440 that can be configured to measure capacity consumed for a device battery 450, in the method of FIG. 6B, for example. The battery 450 can be connected to device 401, such as via power supply circuitry 455, and can be housed together in device 401, or in a battery housing 460 adjacent the device 401, in an example. The controller circuit 405 processes sensor data from the sensor circuitry and calculates battery capacity, such as in the disclosed methods. In an example, the disclosed systems and methods can be used with a leadless device. In an example, one or more satellite electrodes are controlled wirelessly to deliver electrical therapy.

One of the many applications for dynamic battery management systems incorporating one or more teachings of the present subject matter includes an implantable heart monitor, which can also provide therapeutic stimulus to a heart muscle. Thus, for example, an implantable heart monitor can include a pacemaker, a cardioverter/defibrillator, a cardiac resynchronization therapy (CRT) device, a neurostimulator, a congestive heart failure device, or combinations or permutations thereof. An implantable heart monitor can include a lead system, which, after implantation, can electrically contact one or more specified portions of a patient's heart. Portions of the implantable heart monitor can include a monitoring circuit for monitoring heart activity, such as through one or more of the leads of lead system, and a therapy circuit for delivering electrical energy to a heart, such as through one or more of the leads. The implantable heart monitor can also include an energy storage component, which includes a battery and at least one capacitor, in certain examples.

FIG. 5 illustrates a block diagram of a programmer such as illustrated in the system of FIG. 4 or other external device to communicate with the IMD(s), in an example. FIG. 5 illustrates a programmer 544, such as the programmer 430 illustrated in the system of FIG. 4 or other external device to communicate with the implantable medical device(s), in an example. Examples of other external devices include, but are not limited to, Personal Digital Assistants (PDAs), personal laptop and desktop computers, or handheld devices. The illustrated device 544 includes controller circuitry 545 and a memory 546. The controller circuitry 545 can be implemented using hardware, software, or combinations of hardware and software. In an example, the controller circuitry 545 includes a processor to perform instructions in the memory 546, such as to perform a number of functions, including communicating data or programming instructions to the implantable devices. The illustrated device 544 further includes a transceiver 547 and associated circuitry for use to communicate with an implantable device. Various examples can include wireless communication capability. For example, an example of the transceiver 547 and associated circuitry can include an antenna such as for use to wirelessly communicate with an implantable device. The illustrated device 544 further includes a display 548, input/output (I/O) devices 549 such as a keyboard or mouse/pointer, and a communications interface 550 such as for use to communicate with other devices, such as over a communication network. The display 548 can be used to display battery longevity for a battery in the IMD, in an example.

Methods for Battery Measurement Capacity-blending

Figure 6A:
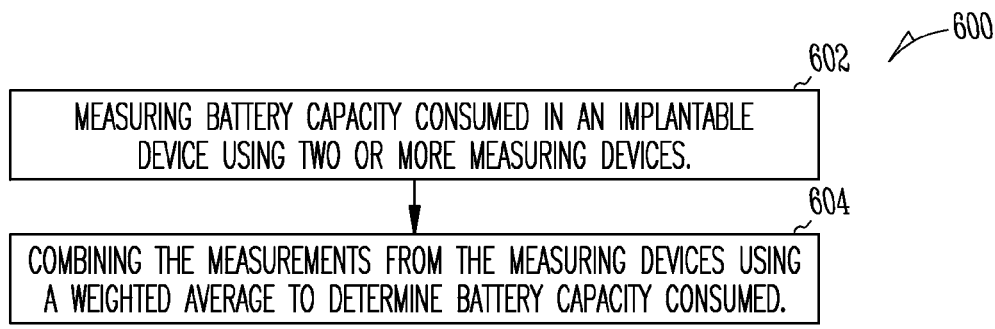
FIG. 6A illustrates a flow diagram of a method of combining measured battery capacity for a battery in an implantable medical device, in an example.

FIG. 6A illustrates a flow diagram of a method of combining measured battery capacity for a battery in an implantable medical device, in an example. In an example of the method 600, battery capacity consumed in an implantable device can be measured using two or more measuring devices, at 602. In an example, the measurements from measuring devices are combined using a weighted average to determine battery capacity consumed, at 604.

In an example, measuring battery capacity consumed includes measuring battery capacity using a coulometer, a capacity-by-voltage device, a software coulometer, or a charge-time measuring device (which can use a look-up table or other technique to convert defibrillation capacitor charge-time to battery capacity consumed or remaining, such as discussed above). Battery capacity consumed can be measured substantially continuously or on an ongoing periodic or recurrent basis, such as, daily, hourly, or in a variety of frequencies, in an example. Battery capacity consumed can be reported to a controller daily, hourly, or in a variety of frequencies, in an example. Measuring battery capacity consumed using a coulometer includes measuring battery capacity using a coulometer that can be calibrated for accuracy, in an example. In an example, measuring battery capacity consumed includes measuring battery capacity in units of Ampere·hours (Ahr).

Figure 6B:
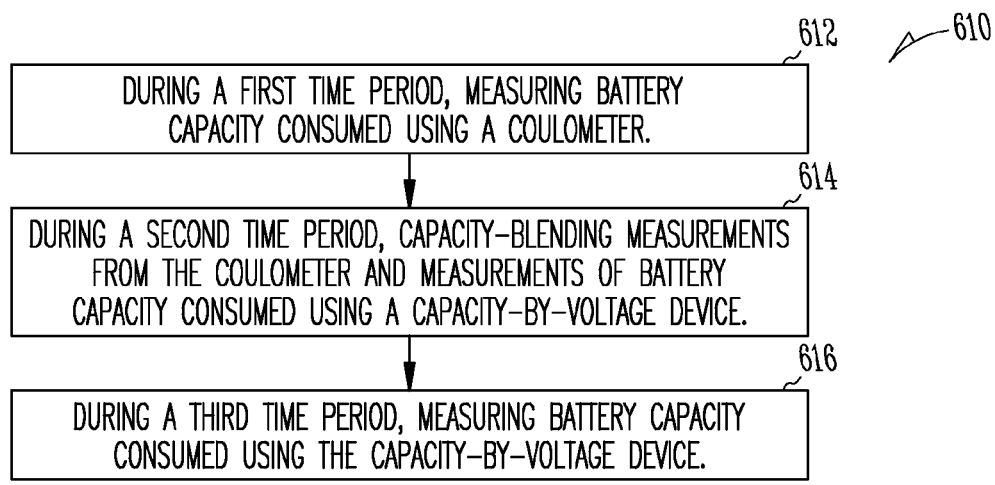
FIG. 6B illustrates a flow diagram of a method for measuring capacity consumed for a battery in an implantable medical device, in an example.

FIG. 6B illustrates a flow diagram of a method for measuring capacity consumed for a battery in an implantable medical device, in an example. In an example of the method 610, battery capacity consumed can be measured using a coulometer during a first time period, at 612. Measurements from the coulometer and measurements of battery capacity consumed using a capacity-by-voltage device are capacity-blended during a second time period, at 614. Battery capacity consumed can be measured using the capacity-by-voltage device during a third time period, at 616.

In an example, the first time period begins at the beginning of life of the battery and ends when the battery has 50% capacity consumed. The second time period begins when the battery has 50% capacity consumed and ends when the battery has 75% capacity consumed, in an example. In an example, the third time period begins when the battery has 75% capacity consumed and ends when the battery capacity expires. Other measures can be used to define the time periods, without departing from the scope of this disclosure. As discussed above, capacity-blending measurements from the coulometer and the capacity-by-voltage device can include computing a weighted average of the measurements in an example. The computed weighted average includes a linear weighted average, in some examples. In an example, measuring battery capacity consumed using the capacity-by-voltage device includes using a look-up table that relates battery voltage to battery capacity consumed.

Methods for Displaying Battery Longevity

Figure 6C:
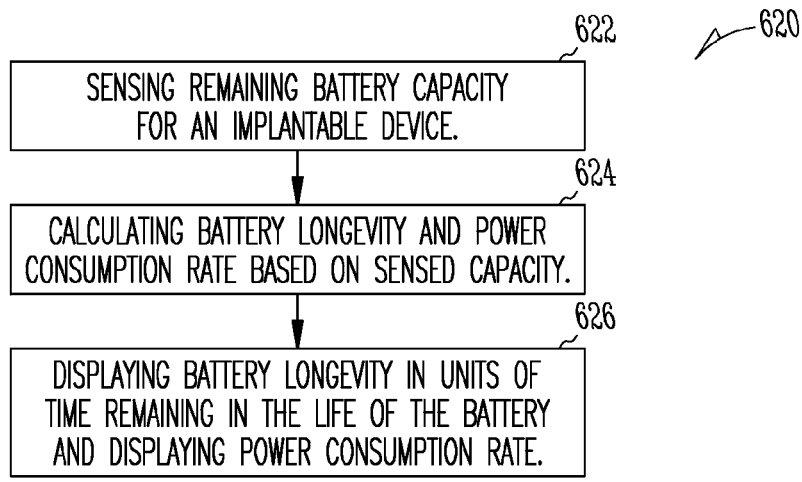
FIG. 6C illustrates a flow diagram of a method for displaying battery longevity for a battery in an implantable medical device, in an example.

FIG. 6C illustrates a flow diagram of a method for displaying battery longevity for a battery in an implantable medical device, in an example. In an example of the method 620, remaining battery capacity for an implantable device can be sensed, at 622, and battery longevity calculated based on the sensed capacity, at 624. Battery longevity can be displayed in units of time remaining in the life of the battery such as in the form of a semi-circular gauge, at 626.

In an example, the method also includes calculating power consumption rate using a coulometer, and displaying the power consumption rate. In an example, sensing remaining battery capacity includes using a coulometer to measure capacity. Sensing remaining battery capacity includes using a capacity-by-voltage device to measure capacity, in an example. In an example, sensing remaining battery capacity includes using a capacity-by-voltage device and a coulometer to measure capacity. In an example, the measurements from the capacity-by-voltage device and the coulometer are capacity-blended to determine battery capacity consumed. In an example, the method also includes calculating battery life phase from sensed capacity.

Figure 6D:
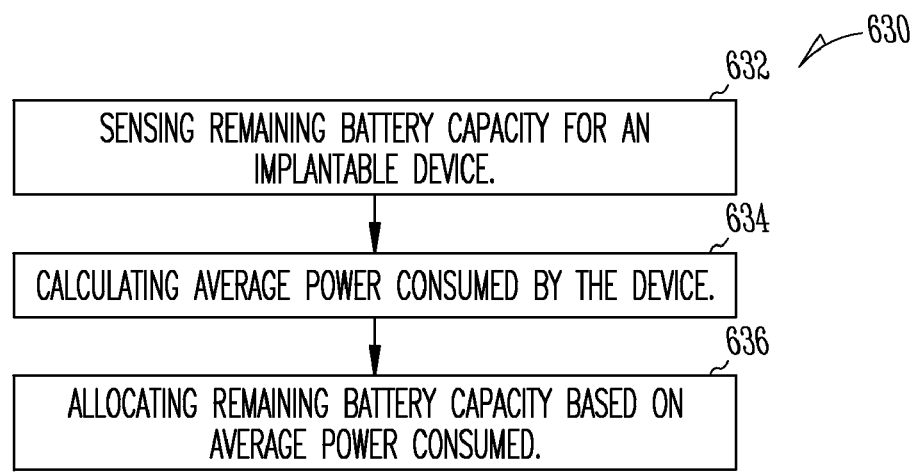
FIG. 6D illustrates a flow diagram of a method for dynamically allocating capacity for a battery in an implantable medical device, in an example.

FIG. 6D illustrates a flow diagram of a method for dynamically allocating capacity for a battery in an implantable medical device, in an example. In an example of the method 630, remaining battery capacity can be sensed for an implantable device, at 632. An average or other central tendency of power consumed by the device can be calculated at 634, in an example. In this example, remaining battery capacity can be allocated based on average power consumed, at 636. In an example, calculating average power consumed includes reporting average power consumed recurrently or periodically, such as daily, hourly or weekly.

In an example, average power consumed can be used to create a dynamic system that allocates battery capacity between an explant indicator (in units of measured capacity) and cessation of therapy. The display provides feedback to a clinician so that the clinician can observe the decreased device longevity resulting from overly aggressive programming, in an example.

Figure 8A:
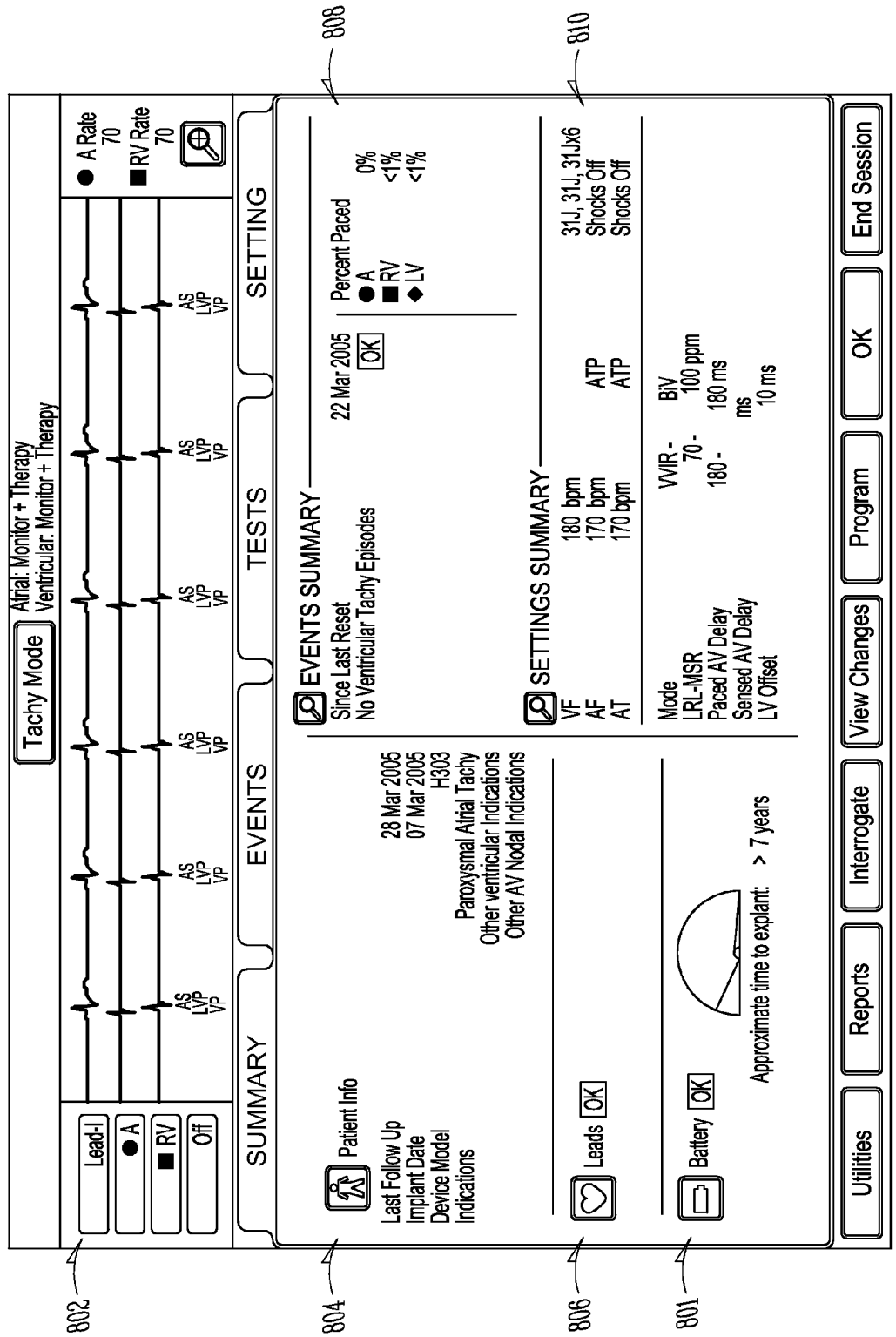
Figure 8B:
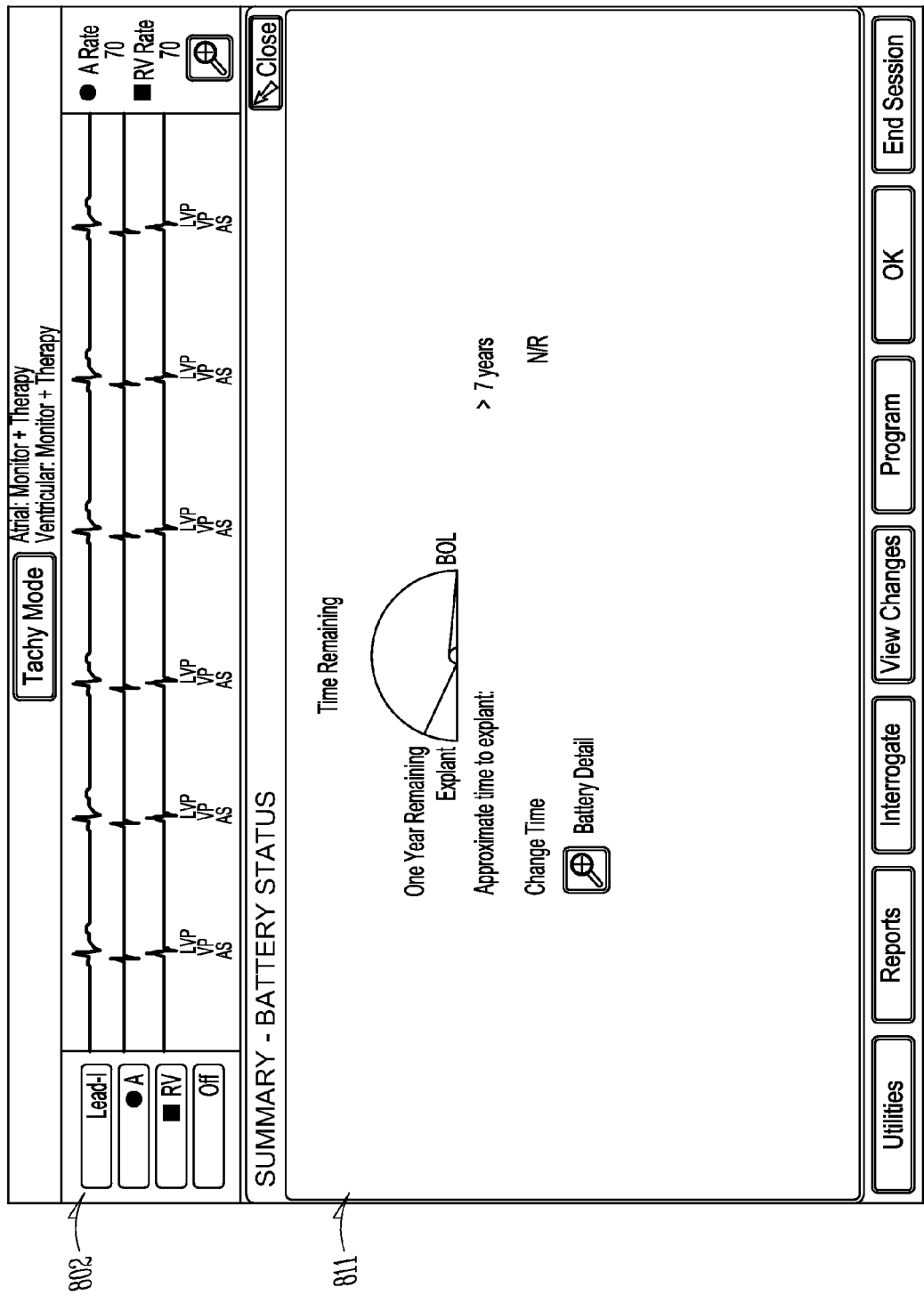
Figure 8C:
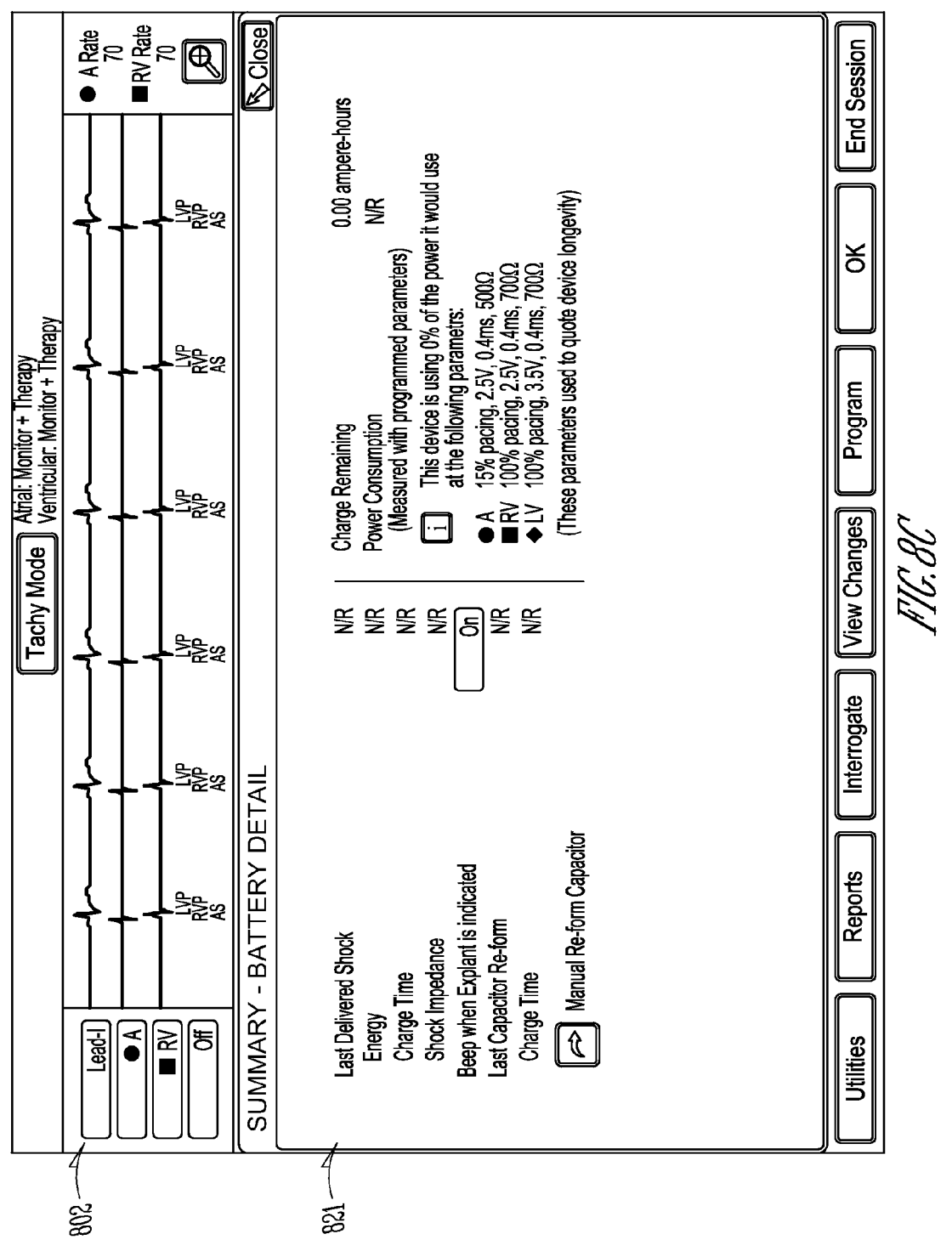
Figure 8D:
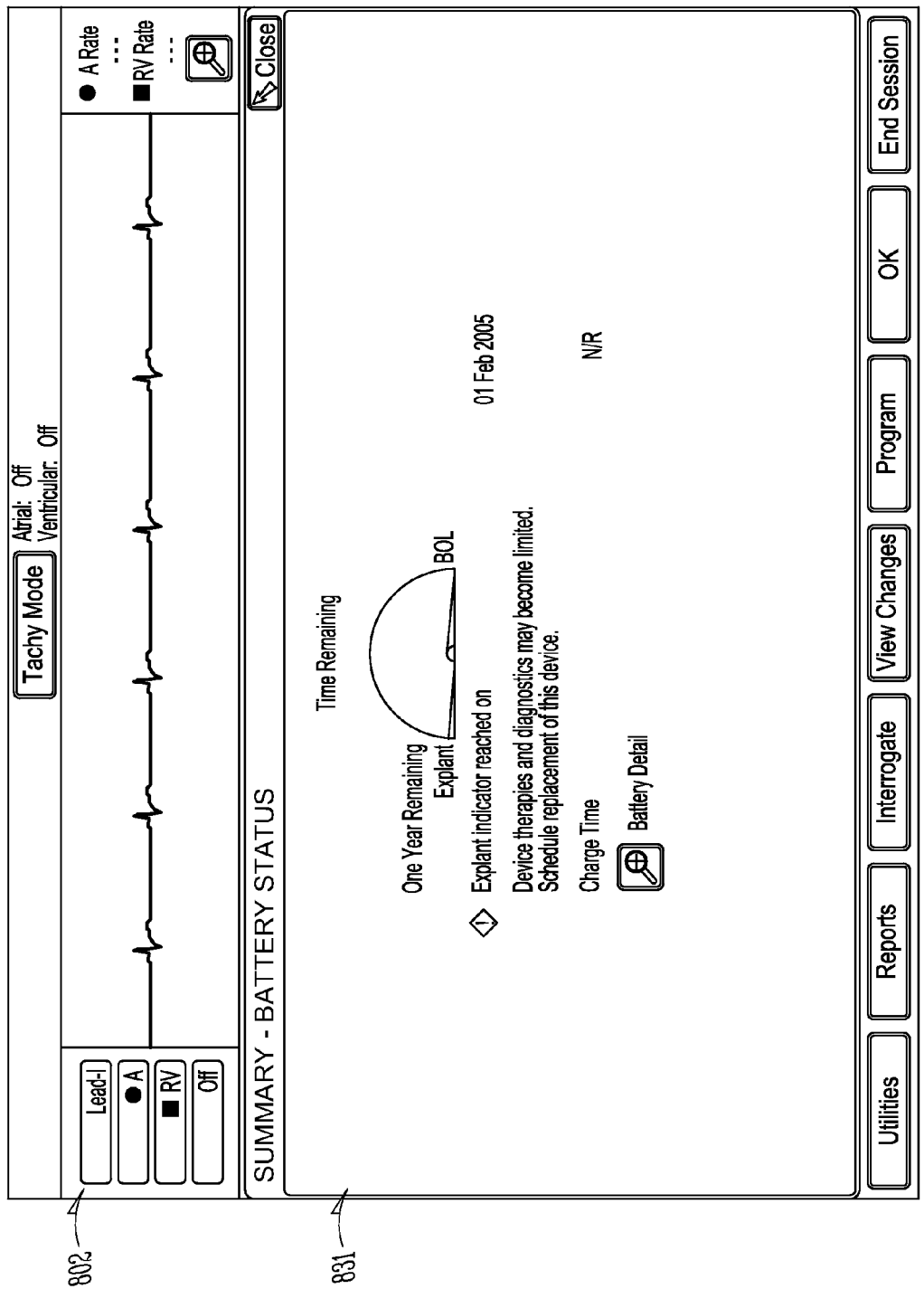

FIGS. 8A-8E illustrate screen displays for the system of FIG. 3, used to display battery longevity, in an example. As discussed with respect to the method of FIG. 6C, battery longevity can be displayed in units of time remaining in the life of the battery. FIG. 8A illustrates a screen display including a lead signal display 802, a patient information display 804, a lead status display 806, a battery status display 801, an events summary display 808, and a settings summary display 810. In this example, the battery status display 801 includes a "gas gauge" type (or semi-circular gauge) graphic 803 with a needle to depict the battery longevity. Battery longevity can be also displayed with text 805, conveying the remaining battery life in units of time. The battery status display 801 further includes a button for battery status, in an example. Other types of battery longevity displays are within the scope of this disclosure. FIG. 8B illustrates a screen display of battery status screen 811 including the lead signal display. FIG. 8C illustrates a screen display of battery detail screen 821. The battery detail screen 821 shows average power and capacity consumed, in an example. Lead signal display 802 can be also depicted. FIG. 8D illustrates a battery status screen 831 including a one-year to explant indicator, similar to the screen of FIG. 8B. In FIG. 8D, however, the gauge indicates that the battery has reached its explant indicator.

Figure 8E:
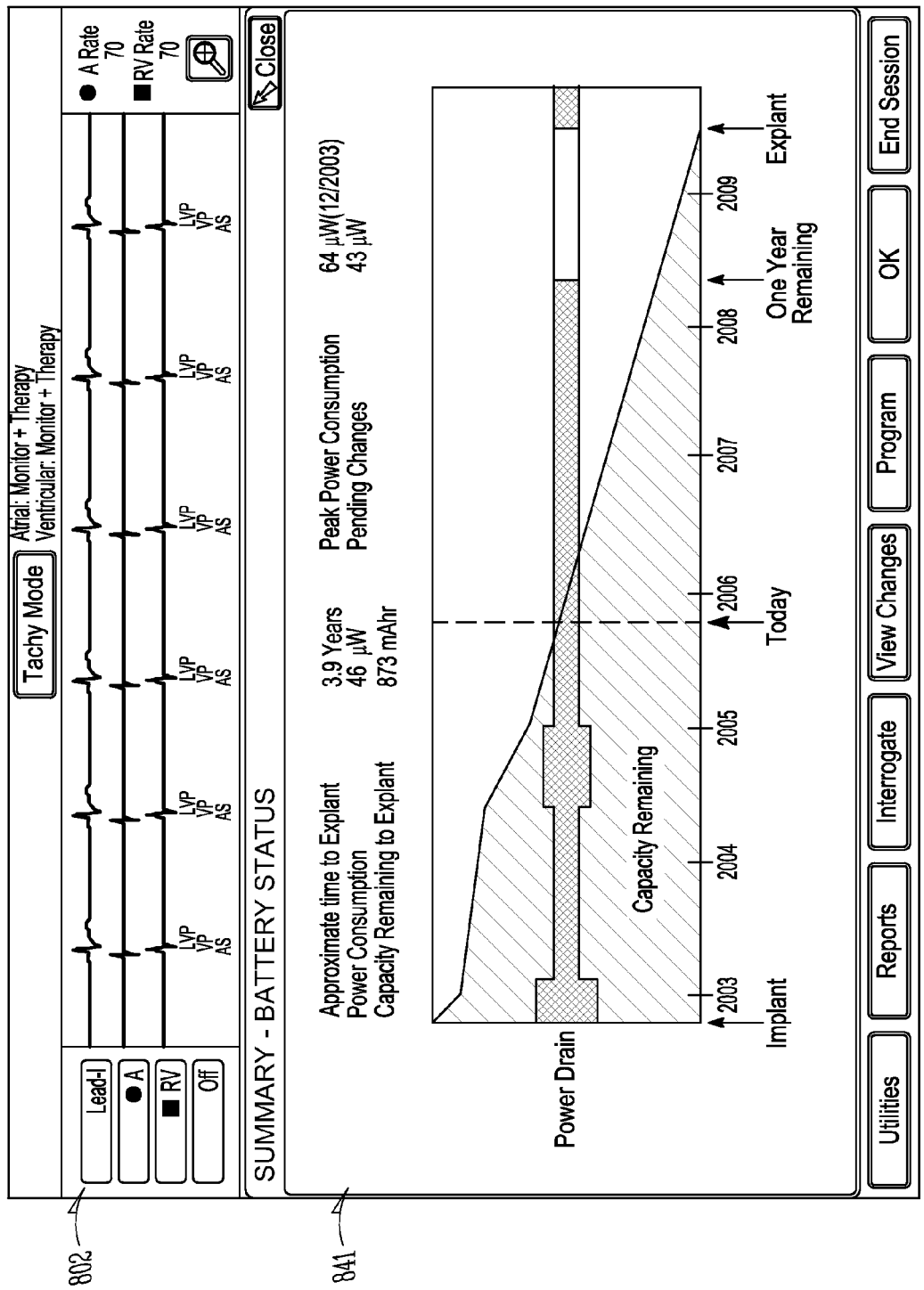

FIG. 8E illustrates a screen display of battery status screen 841, where the battery capacity remaining can be depicted in graphic format. The graph includes a rectangular timeline with the left side indicating implant and the right explant. In addition, a present status indicator and a 1-year to explant indicator are included, in an example. In addition, thickness of a line on the graph can be used to indicate the rate of power consumption, in an example. A cumulative capacity remaining line chart can also be included, and can change dynamically in response to programming changes to show predicted or future power consumption and time to explant. Other shapes and types of battery longevity displays are within the scope of this disclosure.

Abnormal Battery Depletion Detection

In normal operation, the device can use blending of coulometer and battery voltage measurements to estimate battery longevity, or time-to-explant. If a high-current depletion fault exists, however, and if the high current path bypasses or saturates the coulometer, the coulometer may no longer measure charge consumption accurately. In an example, this high current depletion fault can be detected as a voltage-fault condition as indicated by a drop in battery voltage violating an alarm threshold battery voltage value. One or more such alarm threshold battery voltage values can be determined considering one or more of measured battery voltage, battery capacity, possible errors in battery voltage measurement, or possible errors in battery capacity measurement. Over the life of the battery, more than one alarm threshold battery voltage value may be used, such as corresponding to different portions of the battery life. In certain examples, this can improve sensitivity or specificity of the alarms.

Figure 9:
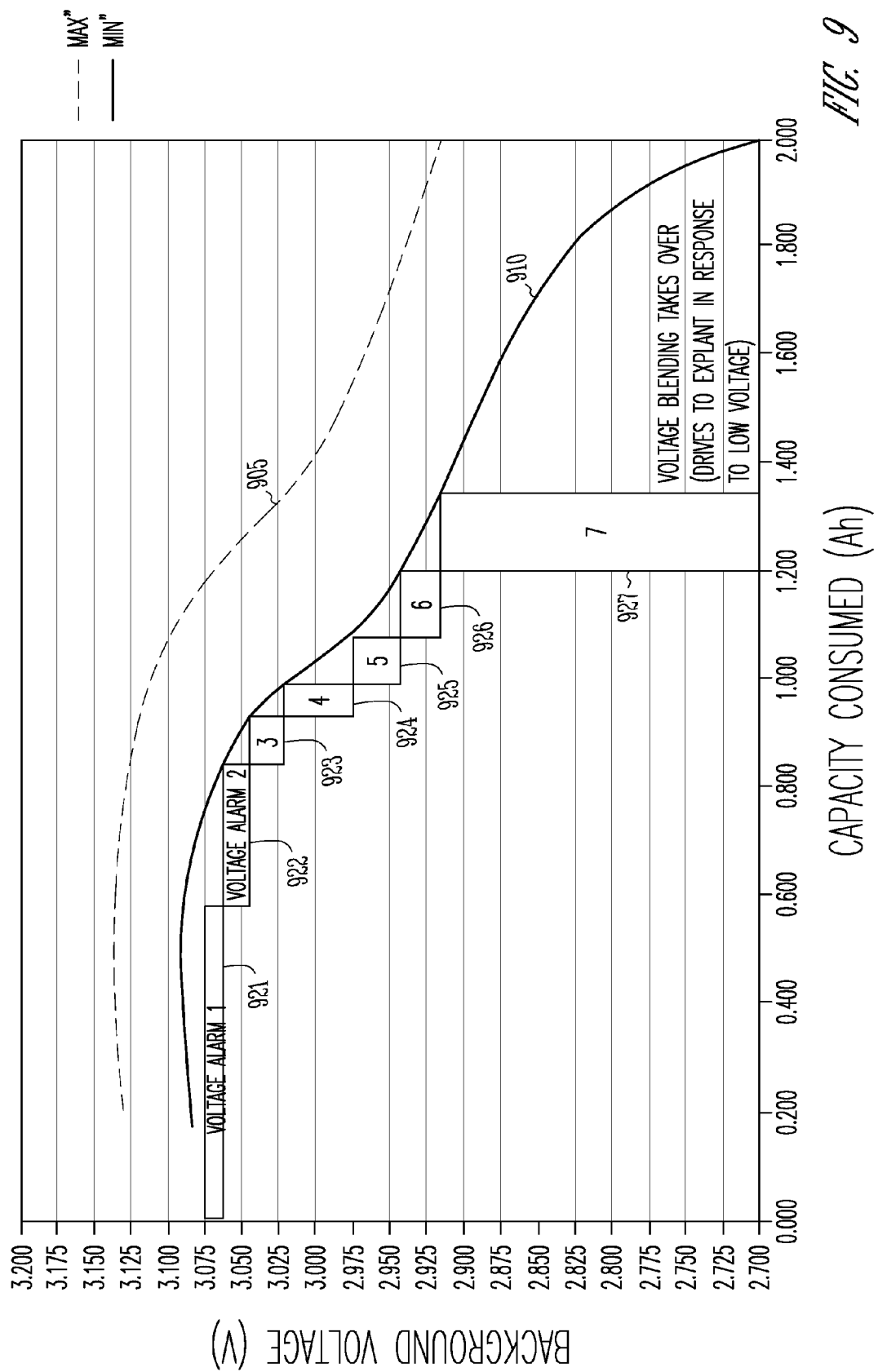
FIG. 9 illustrates a graphical diagram of voltage alarm thresholds for abnormal battery depletion detection in an implantable medical device, in an example.

FIG. 9 illustrates a graphical diagram of battery voltage (V) vs. battery capacity (Ahr) providing an example of battery voltage alarm thresholds for abnormal battery depletion detection in an implantable medical device, in an example. A maximum battery voltage 905 and minimum battery voltage 910 are depicted, along with a number of voltage alarms 921, 922, 923, 924, 925, 926 and 927. While this example provides seven different alarm thresholds over the course of the life of the battery, other numbers of alarms can be used. Different alarm voltage thresholds are used as the battery voltage changes over the life of the battery (shown as battery capacity is consumed). Switching from using one threshold to another can be determined using the blended battery capacity consumed measurements discussed above. In an example, for the first 50% of capacity consumed, the coulometer measures battery capacity consumed. Between 50% and 62.5% of battery capacity consumed, a blend of coulometer and voltage measurements are used, preventing an error if the voltage drops and the coulometer is not functioning properly.

Battery production variations will generally yield an expected range of battery voltage versus battery capacity characteristic curves. The depicted example in FIG. 9 uses nominal minus one standard deviation for the minimum voltage 905, and nominal plus one standard deviation for the maximum voltage 910. Since voltage measurements for an implantable device can have a specified error in the measurement, the minimum voltage 910 can be further adjusted downward by the specified error (e.g., 20 mV) and the maximum voltage 905 can be further adjusted up by the specified error (e.g., 20 mV). Device capacity measurement also has a specified error in the measurement that can be taken into account when generating the voltage thresholds. For the depicted example, the minimum voltage 910 curve was scaled toward the left (less capacity) by 10% and the maximum voltage 905 curve was scaled toward right by 10%, to account for an exemplary error in battery capacity measurements. Because there is no known failure mode that will cause a higher-than-expected battery voltage, a battery voltage alarm need only be generated if the battery voltage falls below the minimum voltage 910. A resulting alert or alarm can be telemetrically or otherwise externally provided, such as locally (e.g., to the patient or another user), or remotely (e.g., over a communication network to a monitoring device available to a caregiver or other user).

To reduce or minimize false alarms, the alarm battery voltage threshold can be set below the minimum voltage 910, in certain examples. To increase or maximize sensitivity, the alarm battery voltage threshold can be set higher, for example, as close to the minimum voltage 910 as possible. While alarm implementation can be simplified by using a small number of different alarm battery voltage thresholds (e.g., one or two) over different portions of the battery's life, better performance can be achieved using more thresholds, or by using a substantially continuous or other function for calculating the alarm battery voltage thresholds, for example, as a function of battery capacity. In certain examples, a device uses two independently specifiable alarm battery voltage thresholds for battery voltage depletion detection, but has built-in capability for five independently specifiable alarm battery voltage thresholds. FIG. 9 shows an example with seven independently specifiable alarm battery voltage thresholds. For the first 0.60 Ahr, the voltage threshold 921 can be 3.075 Volts. The second threshold 922 can be in effect from 0.60 Ahr to 0.85 Ahr and has a threshold of 3.060 Volts. In an example, two of two daily battery voltage measurements in violation of the alarm battery voltage threshold value triggers the alarm. In another example, a single battery voltage measurement in violation of the alarm battery voltage threshold value triggers the alarm.

Figure 10:
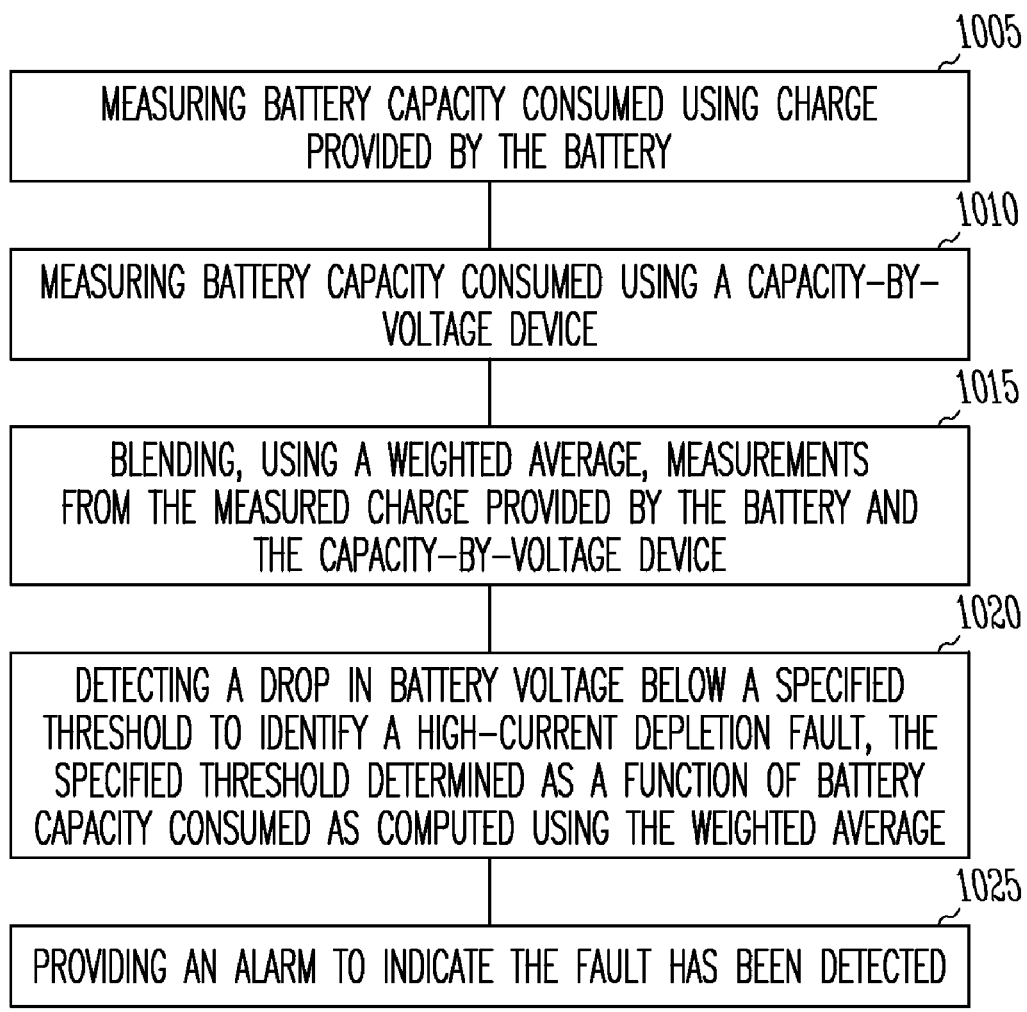
FIG. 10 illustrates a flow diagram of a method for abnormal battery depletion detection in an implantable device, in an example.

FIG. 10 illustrates a flow diagram of a method for abnormal battery depletion detection in an implantable device, in an example. In an example, at 1005 battery capacity consumed can be measured using charge provided by the battery (such as by a coulometer, in an example) and, at 1010 battery capacity consumed can be measured using a capacity-by-voltage device. At 1015, the measurements are blended to determine battery status. At 1020, a drop in battery voltage below one or more programmable thresholds can be detected to identify a high-current depletion fault, and at 1025, an alarm can be provided to indicate the fault has been detected, in an example. The alarm can be provided locally to a patient or remotely over a communication network, such as over a wireless network. To detect a drop in voltage below a threshold, voltage can be measured and compared to the threshold daily or more than once daily, in an example. In an example, the alarm can be provided when at least two battery voltage measurements are below the one or more programmable thresholds. Low voltage measurements due to voltage recovery from a non-fault high current draw condition are suppressed to avoid false alarms. Switching from using one threshold to another can be based upon blended battery capacity consumed measurements. The thresholds can be calculated using a substantially continuous function, or other function. In an example, the thresholds are set below the minimum voltage to reduce false alarms. The coulometer measures batter capacity includes continuously and reports capacity consumed daily in units of Ampere-hours (Ahr), in an example.

The system of FIG. 1 can be adapted for abnormal depletion detection in an implantable device. An example of the system 100 includes a coulometer (device 102) configured to measure capacity of the battery 108 and a capacity-by-voltage device (device 104) configured to use a sensed battery voltage to measure battery capacity. A controller 106 connected to the coulometer and the capacity-by-voltage device can be configured to combine the measurements from the coulometer and the capacity-by-voltage device, using a weighted average to determine battery capacity consumed. The controller 106 can be configured to detect a drop in the sensed battery voltage below a specified threshold to identify a high-current depletion fault. In an example, the controller can be further configured to provide an alarm to indicate the fault has been detected. The alarm can include a message provided on display 110, in an example. The specified threshold can be determined as a function of battery capacity consumed, can include different thresholds corresponding to different portions of battery life, and can be calculated using a substantially continuous or other function, which can be based at least in part upon blended battery capacity consumed measurements. In an example, the one or more programmable thresholds decrease in voltage over the battery life and can include at least seven separate threshold values. Other numbers of threshold values are possible without departing from the scope of this disclosure.

The use of voltage thresholds for triggering alarms can consider causes of low voltage conditions that would not warrant the triggering of an alarm (e.g., false positives). An example of one such condition is voltage recovery of the device. Power draw from the battery can transiently depress the battery voltage. A high voltage charge can depress the measured battery voltage for hours or days. The voltage measurement procedure described above can include detecting and suppressing low voltage measurements that are due to voltage recovery from a non-fault high current draw condition. A voltage recovery procedure can be designed to blank low voltage for known reasons, and to filter voltage for noise. A side-effect of the filtering can be a delay in reporting measured voltage to the rest of the system. Voltage recovery can add a delay of up to three days, in an example. In an example, voltage and capacity measurements are taken daily. In some examples, measurements for abnormal battery depletion detection occur daily.

In an example, battery status can be determined by measuring battery capacity (e.g., using a coulometer) for a first portion of the life of the battery (wherein the "first portion" of the life of the battery can be also measured using a battery capacity determination, such as a coulometer). The above-described battery voltage alarms can be used during this first portion of the battery life, such as to detect an abnormal high-current fault condition that may bypass the coulometer. In this example, during the last portion of the life of the battery, battery status can be determined by using a battery voltage measurement, and thus, use of one or more separate battery voltage alarms can be generally less important during this latter portion of the battery life. As the battery voltage decreases during this latter portion of battery life, a battery status indicator can move to "explant" and then to "end-of-life" (EOL). Declaring a battery voltage fault near explant or EOL can be of less benefit to the patient or clinician as the device will likely be replaced anyway at this time.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the follow-

We claim:

1. A system, comprising:
    a coulometer configured to measure battery capacity;
    a capacity-by-voltage device configured to use a sensed battery voltage to measure battery capacity;
    a controller, coupled to the coulometer and the capacity-by-voltage device, the controller configured to combine the measurements from the coulometer and the capacity-by-voltage device, using a weighted average of both of the measurements to determine battery capacity consumed, wherein a weight of each measurement in the weighted average is based on capacity remaining of the battery; and
    wherein the controller is configured to detect a drop in the sensed battery voltage below one or more specified thresholds to identify a high-current depletion fault, the one or more specified thresholds determined as a function of battery capacity consumed as computed using the weighted average.

2. The system of claim 1, wherein the controller is further configured to provide an alarm to indicate the fault has been detected.

3. The system of claim 1, wherein the one or more specified thresholds include different thresholds corresponding to different portions of battery life.

4. The system of claim 3, wherein the controller is configured to calculate the different thresholds using a substantially continuous function.

5. The system of claim 4, wherein the battery capacity consumed is provided as an input to the substantially continuous function.

6. The system of claim 3, wherein the one or more specified thresholds decrease in voltage over the battery life.

7. The system of claim 3, wherein the different thresholds include at least seven separate threshold values.

8. A method for detecting abnormal depletion for a battery in an implantable medical device, the method comprising:
    measuring battery capacity consumed by measuring an amount of charge provided by the battery;
    measuring battery capacity consumed using a capacity-by-voltage measurement;
    blending, using a weighted average, measurements from the measured amount of charge provided by the battery and the capacity-by-voltage measurement, wherein a weight of each measurement in the weighted average is based on capacity remaining of the battery;
    detecting a drop in battery voltage below one or more programmable thresholds to identify a high-current depletion fault, the specified threshold determined as a function of battery capacity consumed as computed using the weighted average; and
    providing an alarm to indicate the fault has been detected.

9. The method of claim 8, wherein providing an alarm includes providing the alarm locally to a patient.

10. The method of claim 8, wherein providing an alarm includes providing the alarm remotely over a communication network.

11. The method of claim 8, wherein providing the alarm remotely over a communication network includes providing the alarm over an at least partially wireless network.

12. The method of claim 8, wherein detecting a drop in voltage includes measuring battery voltage daily.

13. The method of claim 8, wherein detecting a drop in voltage includes measuring battery voltage more than once daily.

14. The method of claim 13, wherein providing an alarm includes providing an alarm when at least two battery voltage measurements are below the one or more programmable thresholds.

15. The method of claim 8, wherein detecting a drop in voltage includes detecting and suppressing low voltage measurements that are due to voltage recovery from a non-fault high current draw condition.

16. The method of claim 8, further comprising:
    switching from using one threshold to another using one or more blended battery capacity consumed measurements.

17. The method of claim 8, wherein detecting a drop in battery voltage below one or more programmable thresholds includes calculating at least one of the thresholds using a substantially continuous function.

18. The method of claim 17, wherein calculating the thresholds includes setting at least one of the thresholds below a minimum voltage.

19. The method of claim 8, wherein measuring battery capacity consumed using a coulometer includes measuring battery capacity substantially continuously.

20. The method of claim 8, wherein measuring battery capacity consumed using a coulometer includes reporting battery capacity daily.

21. The method of claim 8, wherein measuring battery capacity consumed includes measuring battery capacity in units of Ampere-hours (Ahr).

* * * * *